(12) United States Patent
Py

(10) Patent No.: US 6,805,170 B2
(45) Date of Patent: Oct. 19, 2004

(54) METHOD FOR FILLING A VIAL

(75) Inventor: Daniel Py, Larchmont, NY (US)

(73) Assignee: Medical Instill Technologies, Inc., Stamford, CT (US)

( * ) Notice: Subject to any disclaimer, the term of this patent is extended or adjusted under 35 U.S.C. 154(b) by 0 days.

(21) Appl. No.: 10/694,364

(22) Filed: Oct. 27, 2003

(65) Prior Publication Data

US 2004/0083686 A1 May 6, 2004

Related U.S. Application Data

(60) Continuation of application No. 10/393,966, filed on Mar. 21, 2003, now Pat. No. 6,684,916, which is a division of application No. 09/781,846, filed on Feb. 12, 2001, now Pat. No. 6,604,561.
(60) Provisional application No. 60/182,139, filed on Feb. 11, 2000.

(51) Int. Cl.$^7$ .............................. B65B 3/04; B65B 3/24
(52) U.S. Cl. .............................. 141/2; 141/82; 141/85; 141/94; 141/284; 141/285; 141/329; 53/403
(58) Field of Search .......................... 141/2, 18, 82–85, 141/89, 94, 129, 284, 285, 329; 53/403

(56) References Cited

U.S. PATENT DOCUMENTS

| | | | |
|---|---|---|---|
| 2,503,147 A | 4/1950 | Applezweig | |
| 3,092,278 A | 6/1963 | Järnhäll | |
| 3,340,671 A | 9/1967 | Loo | |
| 3,685,248 A | 8/1972 | Godelaine | |
| 4,250,611 A | 2/1981 | Wong | |
| 4,366,912 A | 1/1983 | Matakura et al. | |
| 4,390,111 A | 6/1983 | Robbins et al. | |
| 4,664,275 A | 5/1987 | Kasai et al. | |
| 4,703,781 A | 11/1987 | Meyer et al. | |
| 4,842,028 A | 6/1989 | Kaufman et al. | |
| 5,085,332 A | 2/1992 | Gettig et al. | |
| 5,088,612 A | 2/1992 | Storar et al. | |
| 5,129,212 A | 7/1992 | Duffey et al. | |
| 5,341,854 A | 8/1994 | Zezulka et al. | |
| 5,411,065 A | 5/1995 | Meador et al. | |
| 5,484,566 A | 1/1996 | Gabbard | |
| 5,514,339 A | 5/1996 | Leopardi et al. | |
| 5,549,141 A | 8/1996 | Meador et al. | |
| 5,641,004 A | 6/1997 | Py | |
| 5,816,772 A | 10/1998 | Py | |
| 6,068,150 A | 5/2000 | Mitchell et al. | |
| 6,684,916 B2 * | 2/2004 | Py ............................... | 141/2 |

FOREIGN PATENT DOCUMENTS

| | | |
|---|---|---|
| FR | 2509689 | 7/1981 |
| GB | 500534 | 2/1939 |

* cited by examiner

*Primary Examiner*—Timothy L. Maust
(74) *Attorney, Agent, or Firm*—McCarter & English, LLP

(57) ABSTRACT

A resealable cap for a medicament vial has a base portion formed of vulcanized rubber or like material known for providing a stable environment for the medicament contained within the vial, and a resealable portion overlying the base portion. The resealable portion is made of low-density polyethylene or like material, and can be punctured by a needle or like injection member for dispensing medicament into the vial. Prior to filling, the cap is assembled to the vial and the cap/vial assembly is sterilized. Then, a needle is inserted through the cap and medicament is introduced through the needle and into the vial. Upon withdrawal of the needle, the penetrated region of the cap is fused by laser or direct heat sealing to hermetically seal the needle hole in the cap.

28 Claims, 8 Drawing Sheets

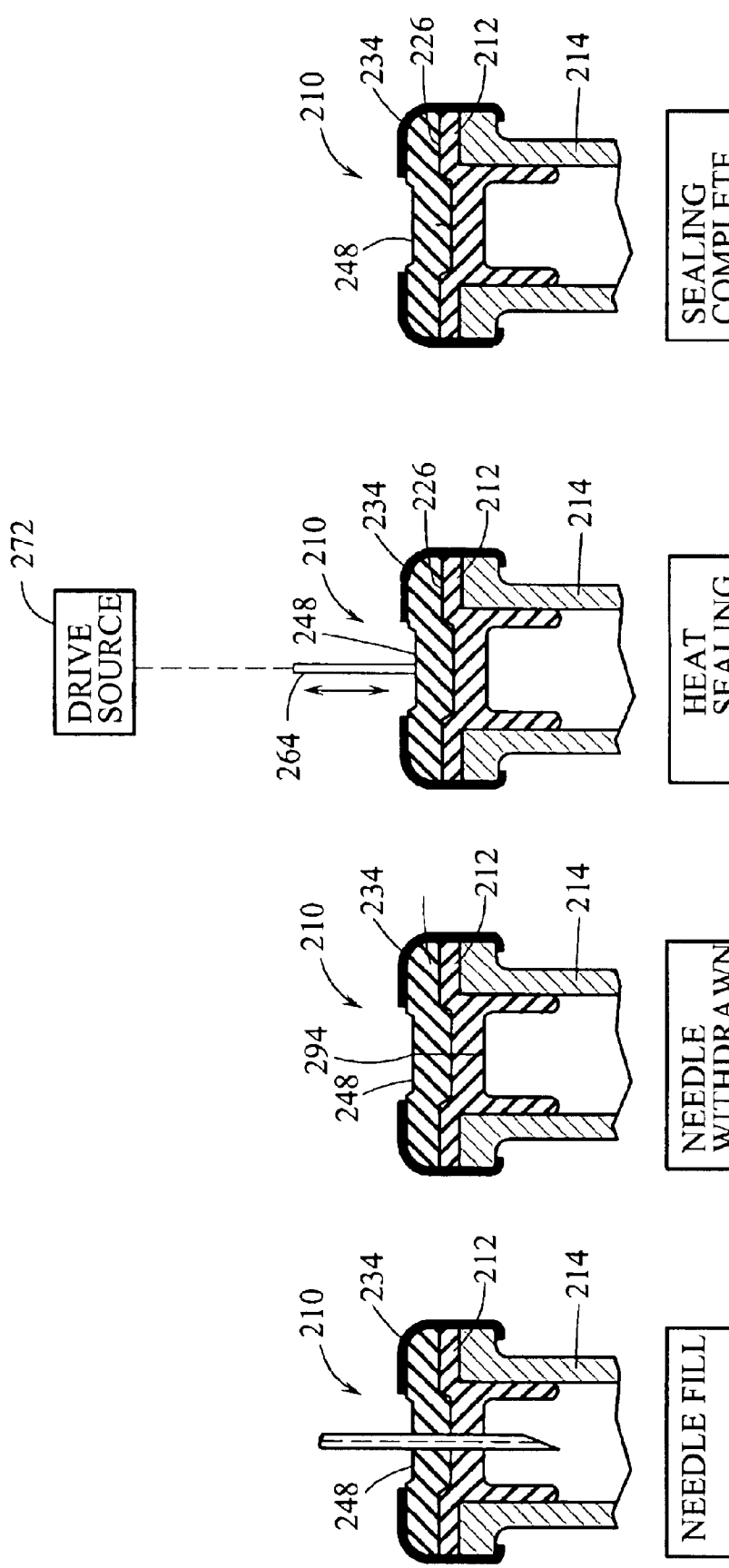

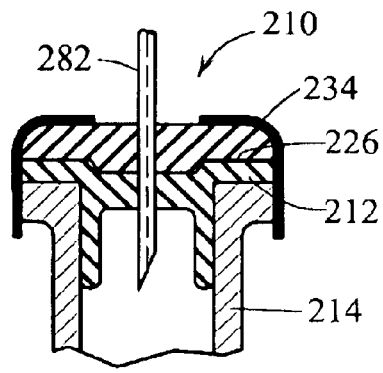
*FIG. 13A*
NEEDLE FILL
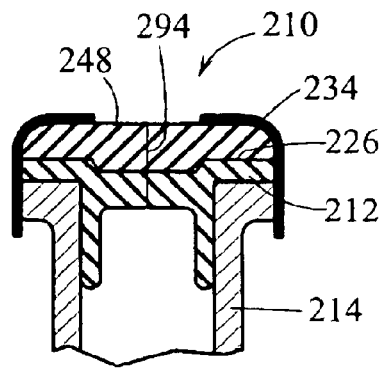
*FIG. 13B*
NEEDLE WITHDRAWN
*FIG. 13C*
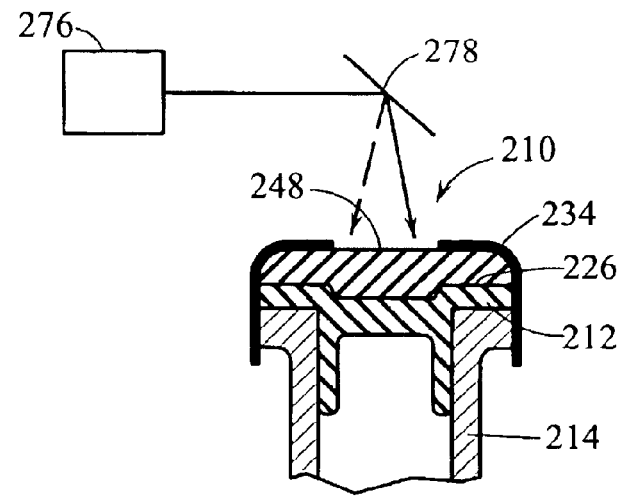
HEAT SEALING

# METHOD FOR FILLING A VIAL

CROSS REFERENCE TO RELATED APPLICATIONS

This application is a Continuation of copending U.S. application Ser. No. 10/393,966, filed Mar. 21, 2003, now U.S. Pat. No. 6,684,916 entitled "Method of Filling a Vial, which is a Division of U.S. application Ser. No. 09/781,846 filed Feb. 12, 2001, now U.S. Pat. No. 6,604,561, entitled "Medicament Vial Having a Heat-Sealable Cap and Apparatus and Method for Filling the Vial"; and claims the benefit of U.S. Provisional Application Ser. No. 60/182,139, filed Feb. 11, 2000, entitled "Heat-Sealable Cap For Medicament Vial", the disclosures of which are hereby incorporated by reference in their entirety as part of the present disclosure.

FIELD OF THE INVENTION

The present invention relates to heat-sealable caps for medicament vials for use where a sterile medicament must be maintained following temporary introduction of a needle or syringe through the cap, and to apparatus and methods for filling such vials.

BACKGROUND OF THE INVENTION

Medicaments such as vaccines are often stored in vials prior to use. Typically, the vials are filled with medicament, and then a cap is installed to seal the medicament in the vial. The cap is typically made of vulcanized rubber or similar resilient material that neither contaminates nor affects the contained medicament. One of the drawbacks associated with this type of filling procedure is that it is difficult to maintain the sterility of the cap during the assembly procedure. In addition, it is difficult to maintain the sterility of the vials and caps during transportation and storage prior to filling.

In order to overcome this contamination risk, the present inventor has determined that it would be desirable to first assemble the cap to the vial, sterilize the assembled cap and vial, such as by irradiation, and then fill the assembled vial by inserting a needle or like injection member through the cap and introducing the medicament through the needle into the sterilized vial. One of the drawbacks associated with this approach, however, is that when the needle or like injection member is inserted through the cap and then withdrawn, it leaves a tiny hole in the cap. The material of the cap is resilient in order to reduce the diameter of the hole, and therefore the hole is usually small enough to keep the medicament from leaking out. However, the hole typically is not small enough to prevent air or other gases from passing through the hole and into the vial, and therefore such holes can allow the medicament to become contaminated or spoiled.

It has been a practice in the pharmaceutical fields to add preservatives to medicaments, such as vaccines, in order to prevent spoilage of the medicaments upon exposure to air or other possible contaminants. Certain preservatives, however, have been determined to cause undesirable effects on patients. Consequently, many medicaments, including vaccines, are preservative free. These preservative-free medicaments, and particularly preservative-free vaccines, are subject to contamination and/or spoilage if contained within a vial wherein the cap has a needle hole as described above.

Vulcanized rubber has been determined to be a safe and effective material for manufacturing vial caps for containing numerous types of medicaments. Many other polymeric materials have not been tested for compatibility with such medicaments, and therefore cannot be used to replace the vulcanized rubber currently used to manufacture caps for medicament vials. Vulcanized rubber, however, is infusible, and therefore any needle holes in such caps are not heat-resealable in situ.

Accordingly, it is an object of the present invention to overcome the above-described drawbacks and disadvantages of the prior art.

SUMMARY OF THE INVENTION

One aspect of the present disclosure is directed to a resealable cap for a medicament vial comprising a base portion formed of vulcanized rubber or like material known for providing a stable environment for the medicament contained within the vial, and a resealable portion overlying the base portion. The resealable portion is made of a resealable polymeric material, such as low-density polyethylene, and can be punctured by a needle or like injection member for dispensing medicament into the vial. Upon removal of the needle, the punctured area of the resealable portion can then be heat sealed to maintain the chamber containing the medicament in a hermetically sealed condition.

Another aspect of the present disclosure is directed to an apparatus and method for filling a resealable vial with a predetermined medicament. The method includes the steps of providing a vial; a resealable cap including a base portion substantially infusible in response to the application of thermal energy thereto, wherein the resealable portion is compatible with the predetermined medicament for exposure to the medicament and for sealing the medicament within the vial; a resealable portion overlying the base portion and being fusible in response to the application of thermal energy thereto; and a locking member engageable with the cap and vial for securing the cap to the vial. Prior to filling the vial with medicament, the resealable cap and locking member are secured to the vial to thereby form a substantially gas-tight seal between the cap and vial. Then, the assembled cap, vial and locking member are sterilized, such as by exposure to beta or gamma radiation. A needle or like injection member is then inserted through the resealable cap and the predetermined medicament is introduced through the needle and into the interior of the vial. In a preferred embodiment of the present invention, the needle is a "double lumen" needle defining a core passageway for the introduction of the predetermined medicament therethrough and into the vial, and an annular passageway coupled in fluid communication with a vacuum source for withdrawing displaced air or other gases or vapors from the interior of the vial. Upon filling the vial with medicament, the needle is withdrawn from the cap, and sufficient thermal energy is applied to the penetrated region of the resealable portion of the cap to fuse the penetrated region and form a substantially gas-tight seal between the penetrated region and the interior of the vial. Preferably, the penetrable region of the resealable member is cauterized, such as by direct heat cauterization or laser cauterization, prior to introducing the needle through the cap, to further ensure the maintenance of sterile conditions throughout the assembly and filling processes.

One advantage of the apparatus and method of the present disclosure, is that the caps and locking members are secured to the vials prior to filling, thus enhancing the ability to maintain sterile conditions throughout the filling process and avoiding the need to assemble the vials in a sterile environment. As a result, the apparatus and method significantly reduce processing time and cost in comparison to prior art vials and filling systems, and moreover, significantly increase the assurance of sterility throughout the assembly and filling processes.

Another aspect of the present disclosure is directed to a resealable stopper and an assembly including the resealable stopper comprising a container, the resealable stopper for sealing a predetermined substance within the container, and a locking member securing the stopper to the container. The resealable stopper includes a body defining a predetermined wall thickness in an axial direction thereof, a needle penetration region that is pierceable with a needle to form a needle aperture therethrough, and is heat resealable to hermetically seal the needle aperture by applying laser radiation from a laser source at a predetermined wavelength and power thereto. The needle penetration region defines a predetermined color and opacity that (i) substantially absorbs the laser radiation at the predetermined wavelength and substantially prevents the passage of the radiation through the predetermined wall thickness thereof, and (ii) that causes the laser radiation at the predetermined wavelength and power to hermetically seal the needle aperture formed in the needle penetration region thereof in a predetermined time period. The assembly further includes a filling machine including a needle for penetrating the resealable stopper and introducing a substance through the stopper and into the container, a substance source coupled in fluid communication to the needle for introducing the substance through the needle and into the container, and a laser source connectable in thermal communication with the resealable stopper for applying laser radiation at the predetermined wavelength and power thereto.

Other advantages of the illustrated embodiment of the present disclosure will become readily apparent in view of the following detailed description and accompanying drawings.

BRIEF DESCRIPTION OF THE DRAWINGS

FIGS. 12A through 12D are somewhat schematic, cross-sectional, sequential views illustrating an apparatus used in, and a method of the present invention for hermetically sealing the penetrated region of the resealable portion of the cap by direct heat sealing after withdrawing the filling needle therefrom.

FIGS. 13A through 13C are somewhat schematic, cross-sectional, sequential views illustrating an apparatus used in, and a method of the present invention for hermetically sealing the penetrated region of the resealable portion of the cap by laser sealing after withdrawing the filling needle therefrom.

DETAILED DESCRIPTION OF THE PREFERRED EMBODIMENTS

Figure 1:
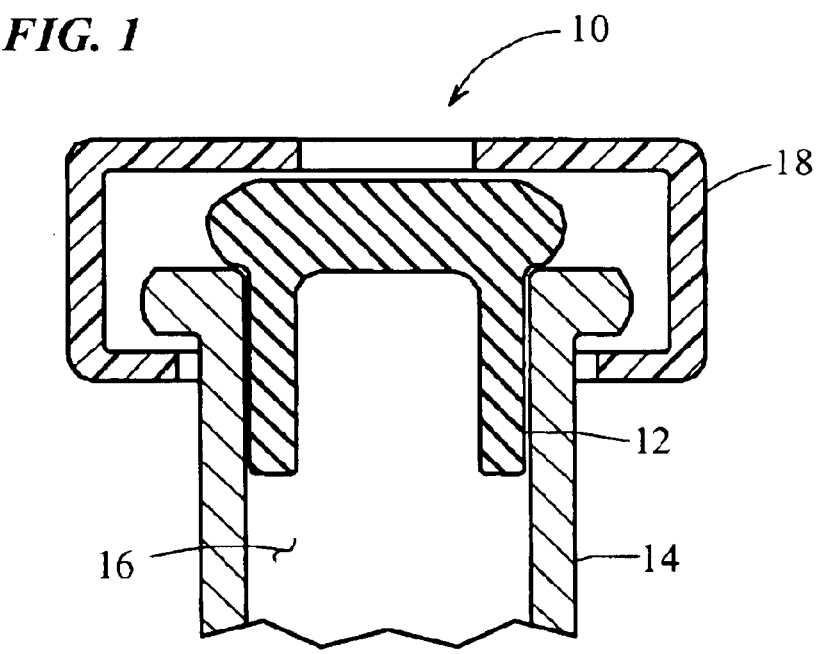
FIG. 1 is a somewhat schematic, partly exploded, cross-sectional view of a prior art end cap for a medicament vial.

As shown in FIG. 1, a prior art cap for a medicament vial is generally designated by the reference numeral 10. The cap 10 includes a vulcanized rubber base 12, which is slidably received within the open end of a vial 14. The vial 14 is made of glass or like material, and it defines a chamber 16 for receiving medicament. An aluminum locking ring 18 surrounds the periphery of the cap 12 and vial 14, and it is crimped in place to lockably connect and seal the cap to the vial.

In operation, a hypodermic needle (not shown) is inserted through the vulcanized rubber base in order to deposit medicament within the chamber 16. Once the medicament has been deposited, the needle is withdrawn from the cap 10. Although the hole resulting from insertion of the needle will shrink somewhat from its maximum diameter due to the resiliency of the vulcanized rubber, the resultant hole is typically still large enough to pass gas or vapor and thereby compromise any preservative-free medicament contained within the chamber 16.

Figure 2:
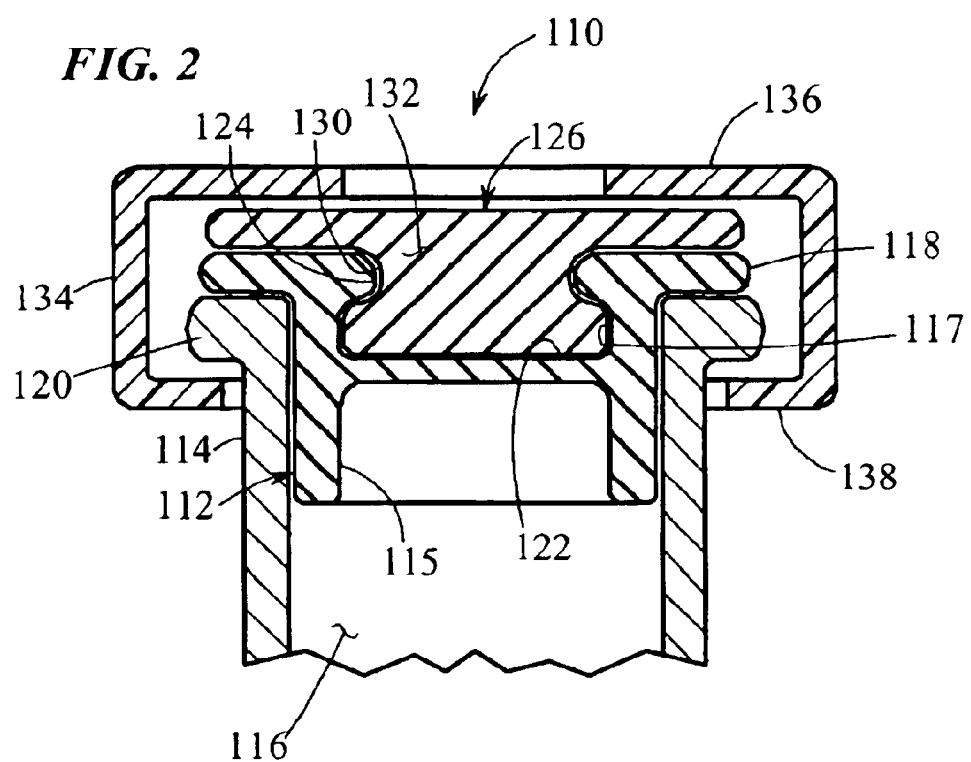
FIG. 2 is a cross-sectional, partly exploded view of a resealable cap used in a method of the present invention.

Turning to FIG. 2, a heat-resealable cap used in a method of the present invention is indicated generally by the reference numeral 110. The cap 110 includes a resilient base 112 made of vulcanized rubber or like material which is known to those of ordinary skill in the pertinent art, and acceptable for use in the manufacture of end caps or the portions thereof placed in contact with, or otherwise exposed to medicaments, such as vaccines. The base 112 defines a lower peripheral wall 115 shaped and dimensioned to be slidably received within the open end of a vial 114. The vial 114 is made of glass or like material, and it defines a chamber 116 for receiving medicament. The base 112 of the cap 110 further defines an upper peripheral wall 117 also shaped and dimensioned to be slidably received within the open end of the vial 114, and a peripheral sealing flange 118 projecting outwardly from the upper end of the peripheral wall 117. The vial 114 is made of glass or other suitable material, and defines at its open end a peripheral flange 120. As shown slighty exploded in FIGS. 2 and 3, the peripheral flange 118 of the base 112 sealingly engages the peripheral flange 120 of the vial 114 to seal the interface between the cap and vial. The base 112 further defines an upper recess 122 formed within the upper peripheral wall 117, and an annular rim 124 projecting inwardly from the upper end of the peripheral wall.

Figure 3:
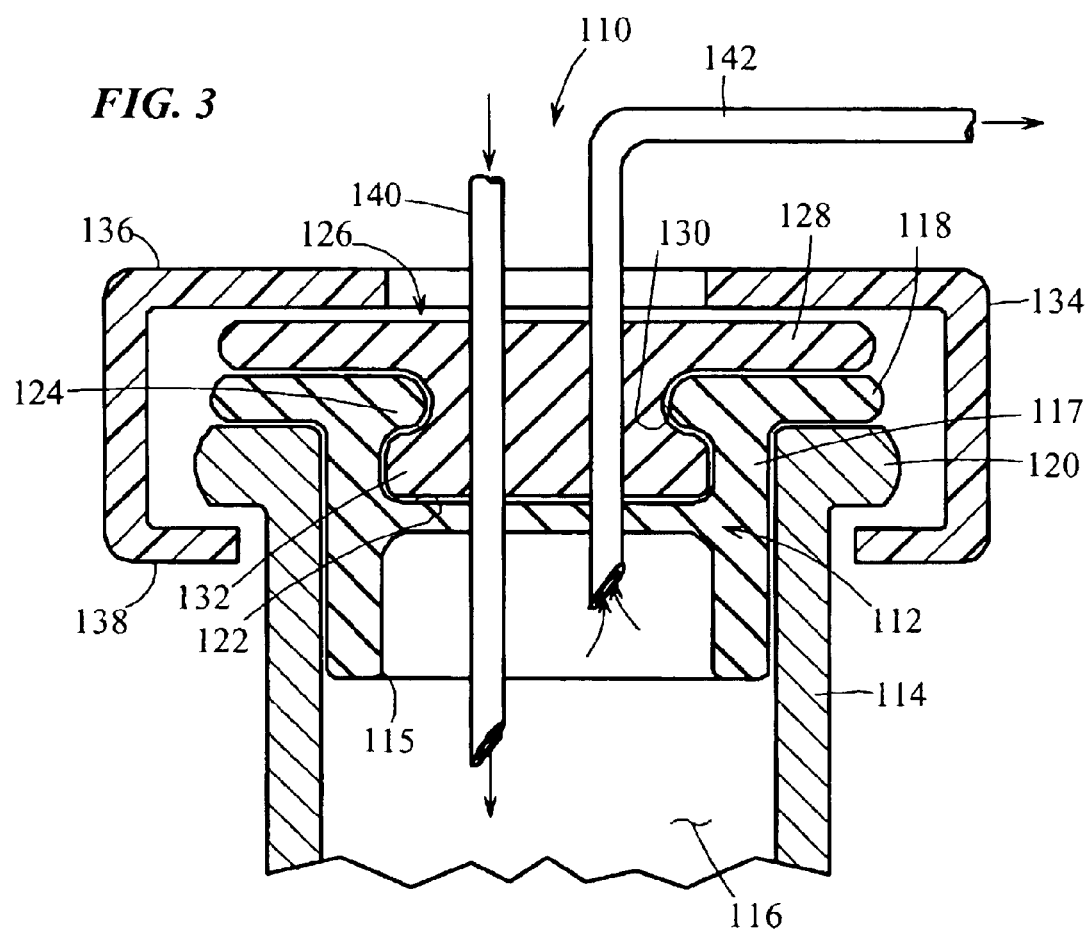
FIG. 3 is a cross-sectional, partly exploded view of the resealable cap of FIG. 2 shown with an injection needle or syringe inserted through the end cap for introducing medicament into the vial, and a venting needle or syringe inserted through the end cap for venting the vial during filling of the medicament.
Figure 4:
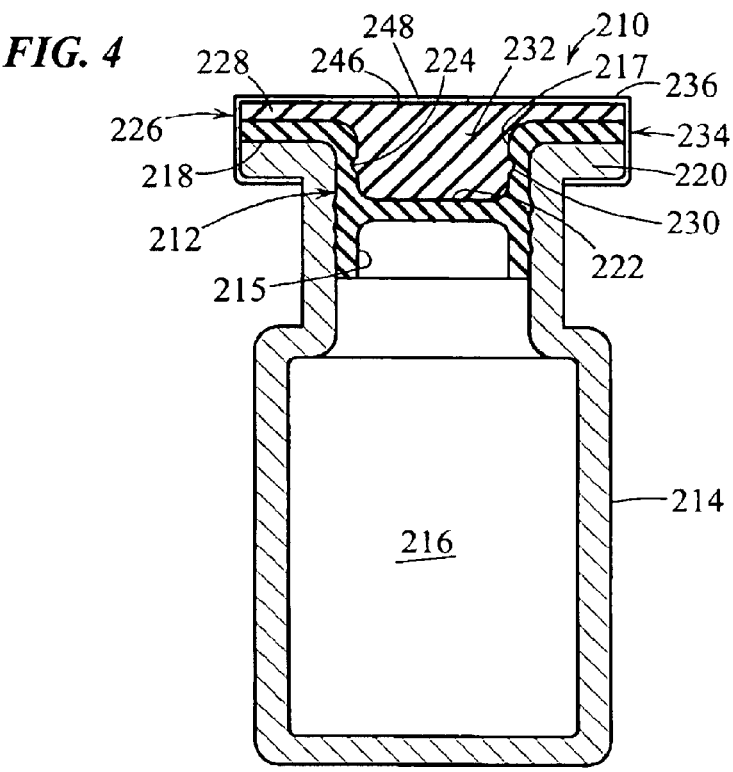
FIG. 4 is a cross-sectional view of another embodiment of the resealable cap and vial used in a method of the present invention.

A resealable member 126 is fixedly received within the upper recess 122 of the base 112 to form the assembled cap 110. The resealable member 126 defines an upper peripheral flange 128, an annular recessed portion or recess 130, and a base 132 located on the opposite side of the annular recess 130 relative to the flange, and projecting outwardly from the recess. As can be seen in FIGS. 2 and 3, the annular recess 130 and base 132 of the resealable member 126 are dimensioned and shaped complementary to (or define the mirror image of) the interior surfaces of the upper recess 122 and annular rim 124 of the base 112. Accordingly, the resealable member 126 is pressed, snapped or otherwise received within the upper recess 122 such that the annular rim 124 is received within the annular recess 130 to thereby fixedly secure the resealable member within the base.

The resealable member 126 is preferably made of a resilient polymeric material, such as a blend of the polymeric material sold by Kraton Polymers and GLS Corporation under the registered trademark KRATON® and a low-density polyethylene, such as the polyethylene sold by Dow Chemical Co. under the trademarks ENGAGE™ or EXACT™. An important feature of the resealable member 126 is that it be resealable to form a gas-tight seal after inserting a needle, syringe or like injection member through the resealable member. Preferably, the resealable member can be sealed by heating the area punctured by the needle in a manner known to those skilled in the pertinent art and described further below. One advantage of the blended polymer described above is that it is known to minimize the degree to which the medicament can be absorbed into the polymer in comparison to KRATON® itself.

An aluminum locking or crimping ring 134 defining an upper peripheral flange 136 and a lower peripheral flange 138 is mounted over the end cap 110 and vial 114. The locking ring 134 is of a type known to those of ordinary skill in the pertinent art for fixedly securing end caps to vials, and may take the shape or form of any of numerous different locking rings which are currently or later become known for performing the functions of the locking ring described herein. The upper and lower flanges 136 and 138, respectively, of the locking ring are crimped or otherwise pressed against the adjacent surfaces of the cap and vial to press the sealing flanges of the cap against the vial and thereby maintain a fluid-tight and/or gas-tight seal between the cap and vial.

As shown in FIG. 3, the heat-resealable cap 110 is shown with a hypodermic or other type of needle 140 inserted through the resealable member 126 and the resilient base 112 in order to dispense medicament into the chamber 116 of the vial. A venting needle 142 is likewise inserted through the resealable member 126 and the resilient base 112 in order to allow gas to escape from the vial 114 as the medicament is deposited into the vial. Preferably, the apparatus and method for dispensing the medicament into the vial is as shown in U.S. Pat. No. 5,641,004 to Daniel Py, issued Jun. 24, 1997, which is hereby expressly incorporated by reference as part of the present disclosure.

In operation, the resealable member 126 is inserted into the base 112, and the assembled end cap 110 is slidably inserted into the open end of the vial 114. The locking ring 134 is then crimped in place to lock the cap 110 to the vial and maintain the gas-tight seal at the interface of the cap and vial. The assembled cap 110 and vial 114 preferably are then sterilized, such as by exposing the assembly to beta and/or gamma radiation in a manner known to those of ordinary skill in the pertinent art. The medicament-dispensing needle 140 is then inserted through the resealable member 126 and the resilient base 112 until the free end of the needle is received into the chamber 116 of the vial to, in turn, dispense medicament into the chamber. The venting needle 142 is likewise inserted through the resealable member 126 and the resilient base 112 in order to draw gas from the sealed vial as the liquid medicament is deposited within the chamber of the vial. Once the medicament has been deposited within the chamber of the vial, the needles 140 and 142 are withdrawn from the cap 110, and as described further below, a heat or other energy source is applied to the portions of the resealable member 126 punctured by the needles 140 and 142 to, in turn, seal the punctured areas and hermetically seal the medicament within the vial.

One advantage of the preferred embodiments of the present invention is that the resealable member 126 of the cap 110 may be resealed following the deposit of medicament into the chamber 116, thereby rendering the end cap of the invention particularly suitable for use with preservative-free medicaments, such as preservative-free vaccines. Accordingly, a further advantage of the preferred embodiments of the present invention is that the medicament need not contain a preservative, and therefore the above-described drawbacks and disadvantages of such preservatives can be avoided.

Another advantage of the preferred embodiments of the present invention is that the medicament within the resealed chamber 116 is not contaminated or otherwise affected by impurities or other agents in the atmosphere where the vial is stored or transported.

Figure 5:
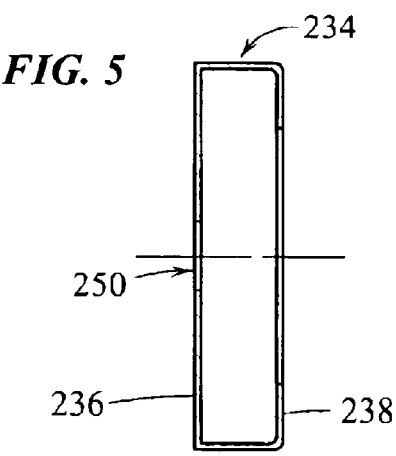
FIG. 5 is a cross-sectional view of the crimpable locking member of FIG. 4 for securing the resealable cap to the vial.
Figure 6:
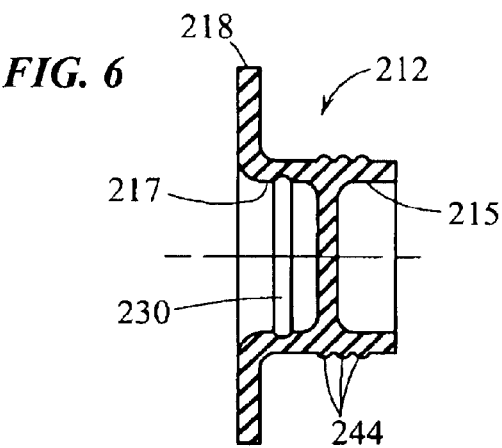
FIG. 6 is a cross-sectional view of the base portion of the resealable cap of FIG. 4 made of a material compatible with the predetermined medicament to be sealed within the vial, such as vulcanized rubber.

In FIGS. 4 through 8 another resealable cap used n a method of the present invention is indicated generally by the reference numeral 210. The resealable cap 210 is essentially the same as the cap 110 described above, and therefore like reference numerals preceded by the numeral "2" instead of the numeral "1" are used to indicate like elements. As shown best in FIGS. 4 and 6, the base 212 of the cap defines on the interior side of its upper peripheral wall 217 an annular groove 230. As shown best in FIGS. 4 and 7, the resealable member 226 defines on the peripheral surface of its base 232 an annular raised portion or protuberance 224 dimensioned to be frictionally received within the corresponding annular groove 230 of the base 212 to thereby secure the resealable member to the base. As shown in FIG. 6, the base 212 further defines on the exterior side of its lower peripheral wall 215 a plurality of raised annular portions or protuberances 244 axially spaced relative to each other for frictionally engaging the interior wall of the vial 214 to thereby secure the cap within the vial and facilitate maintaining a hermetic seal between the cap and vial. As shown best in FIGS. 7 and 8, the resealable member 226 defines on its top surface an annular raised portion or protuberance 246 defining a circular surface portion 248 therein for receiving a filling needle or like instrument, as described further below. As shown in FIG. 5, the locking or crimping ring 234 defines a central aperture 250 in its upper side for receiving therethrough the annular raised portion 246 of the resealable member 226.

Preferably, the resealable cap 210 and vial 214 are assembled and the locking ring 234 is crimped in place as described above and shown in FIG. 4 prior to introducing any medicament or other fluid into the vial. Then, one or more of the empty cap/vial assemblies of the present invention are enclosed, sterilized, and transported in accordance with the teachings of the present inventor's commonly owned U.S. Pat. No. 5,186,772, entitled "Method Of Transferring Articles, Transfer Pocket And Enclosure", which is hereby expressly incorporated by reference as part of the present disclosure. As disclosed in the '772 patent, the empty cap/vial assemblies are placed in an internal bag or "pocket" which is closed and, if desired, provided with a sterilization indicator. Then, the internal pocket is placed within a transfer pocket including a sealing frame defining an annular groove on a peripheral surface thereof. The transfer pocket is stretched over the surface of the frame and closed by an elastic band overlying the transfer pocket and received within the peripheral groove. The transfer pocket likewise may include therein a sterilization indicator. Preferably, the assembled transfer and internal pockets are sealed within an "external" pocket and the assembled pockets are subject to sterilization, such as by exposure to gamma radiation, to sterilize the pockets and the empty cap/vial assemblies within the pockets. The transfer pockets can then be used to store and/or transport the sterilized assemblies to a filling system without contaminating the sterilized assemblies. As further described in the '772 patent, the filling system is located within a sterile enclosure, and the empty vials are introduced into the enclosure by removing and discarding the external pocket, and connecting the sealing frame of the transfer pocket to a window or transfer port of the enclosure. As further disclosed in the '772 patent, an adhesive material is preferably superimposed on the sealing frame for securing the transfer pocket to the transfer port of the filling system enclosure. Prior to releasing the cap/vial assemblies into the filling system enclosure, the sterilization indicators are preferably checked in order to ensure that the sterile condition of the vial/cap assemblies were maintained throughout storage and transfer. As described in the '772 patent, the portion of the transfer pocket overlying the frame is then cut away and simultaneously sterilized along the trimmed surfaces to destroy any microorganisms or germs thereon, and to allow the internal pocket to be received through the transfer port and into the enclosure.

Once received within the enclosure, the internal pocket is opened and the empty cap/vial assemblies are removed and loaded into a filling machine located within the sterile enclosure. Once loaded into the filling machine, the resealable member 226 of each empty cap/vial assembly is preferably sterilized again in order to further ensure that no contaminates enter the vial during the filling process. In accordance with the preferred embodiments of the present invention, the resealable members 226 are sterilized at this stage by either direct heat cauterization or laser cauterization.

Figures 9A, 9B, 9C:
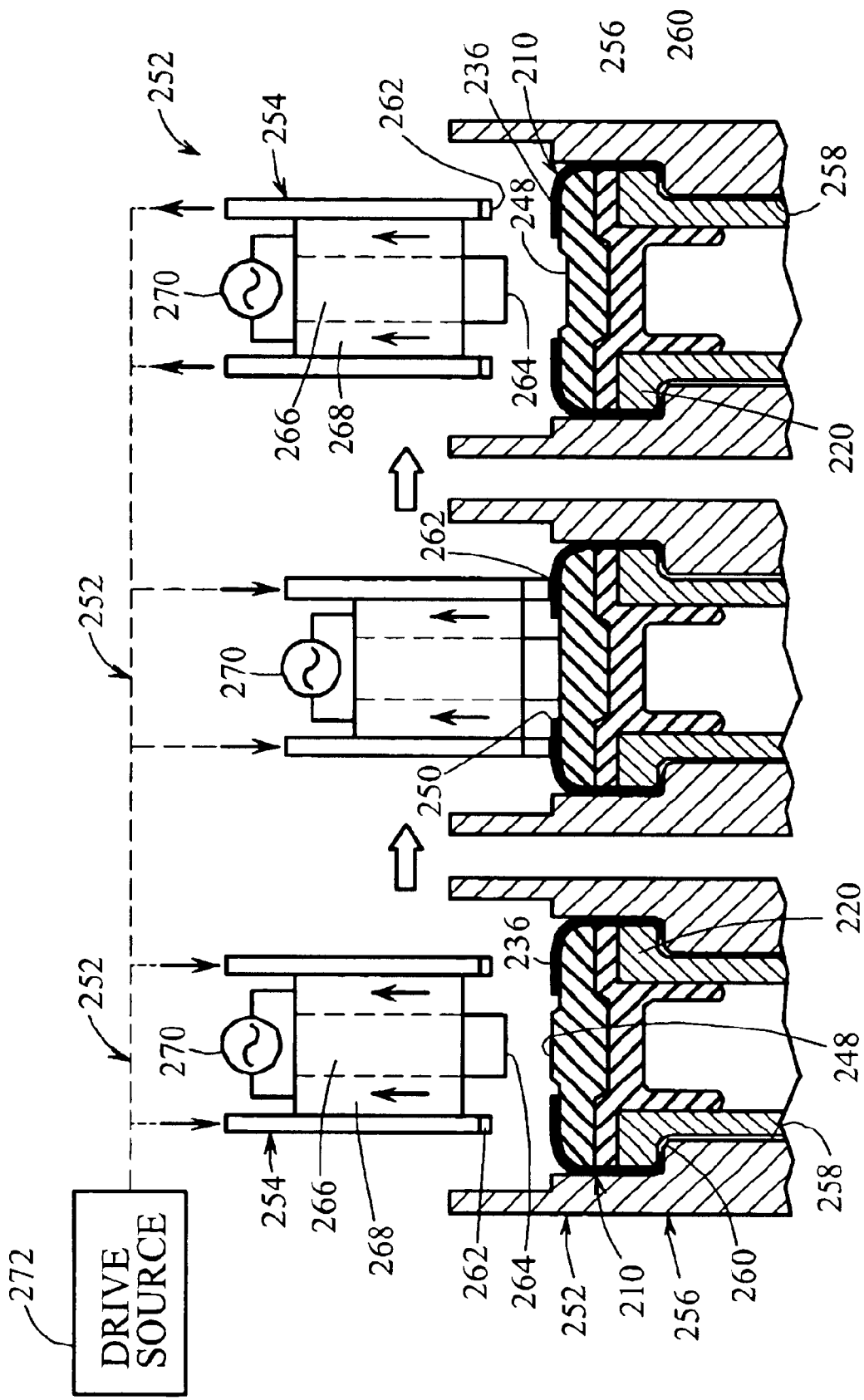
FIGS. 9A through 9C are somewhat schematic, cross-sectional, sequential views illustrating the apparatus and method of the present disclosure for sterilizing the resealable portion of the cap by direct heat cauterization prior to introducing the filling needle or like instrument therethrough.

As shown in FIGS. 9A through 9C, an apparatus for cauterizing the resealable caps by application of heat thereto is indicated generally by the reference numeral 252. The apparatus 252 comprises a housing 254 mounted over a vial support 256. The vial support 256 may be adapted to hold a single vial, or preferably, is adapted hold a plurality of vials. The embodiment of the support adapted to hold a plurality of vials defines a channel 258 for receiving therein the vials, and a pair of opposing shoulders 260 formed at the upper edge of the channel for supporting thereon the flange 220 of the vial. If desired, a vibratory drive (not shown) may be drivingly connected to the support 256 to vibrate the support and, in turn, move the vials through the channel at a predetermined rate. However, as may be recognized by those skilled in the pertinent art based on the teachings herein, any of numerous different drive systems that are currently, or later become known, may be equally employed to move the vials through the filling machine.

The housing 254 defines a peripheral sealing surface 262 formed on the free end of the housing for sealingly engaging the upper flange surface 236 of each locking member 234. As shown best in FIG. 9B, the peripheral sealing surface surrounds the aperture 250 formed through the locking member and exposing the penetrable region 248 of the resealable member 226 of the cap. Preferably, the peripheral sealing surface 262 forms a substantially fluid-tight seal between the housing and the cap. A heating surface 264 projects outwardly from the free end of a central support 266 of the housing for contacting the penetrable surface 248 of the resealable member and cauterizing the surface. An annular conduit 268 extends about the periphery of the heating surface 264 and is coupled in fluid communication to a vacuum source 270 for drawing air through the conduit and away from the cauterized surface 248, as indicated by the arrows in the Figures. The housing 254 is drivingly connected to a drive source 272 for moving the housing and thus the heating surface 264 into and out of engagement with the exposed penetrable surface portion 248 for cauterizing the surface, as indicated by the arrows in the Figures. As may be recognized by those skilled in the pertinent art based on the teachings herein, the drive source 272 may take the form of any of numerous different types of drive sources that are currently, or later become known, for performing the function of the drive source as described herein, such as a pneumatic drive, or a solenoid-actuated or other type of electric drive. Similarly, the heating surface 264 may take any of numerous different shapes and configurations, and may be heated in any of numerous different ways that are currently or later become known, such as by an electric resistance heater (or "hot wire"). Preferably, however, the heating surface 264 defines a surface shape and contour corresponding to the desired shape and contour of the penetrable surface region 248 of the cap.

Figure 7:
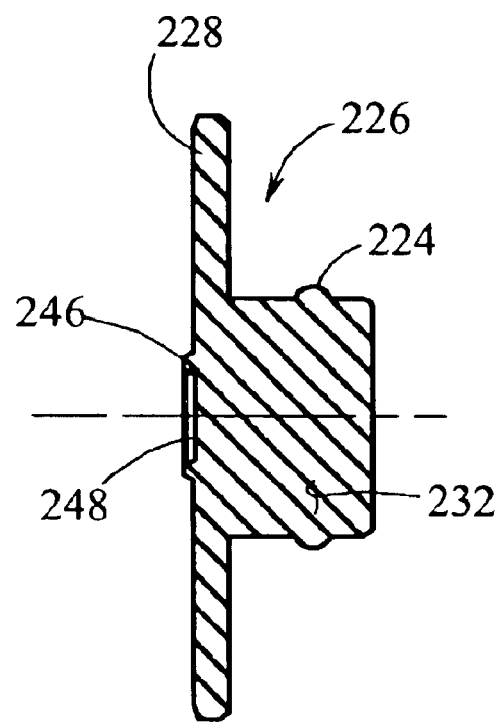
FIG. 7 is a cross-sectional view of the resealable portion of the cap of FIG. 4 formed of a material that is fusible in response to the application of thermal energy thereto in order to hermetically seal the cap after inserting and removing a filling needle or like instrument therethrough.
Figure 8:
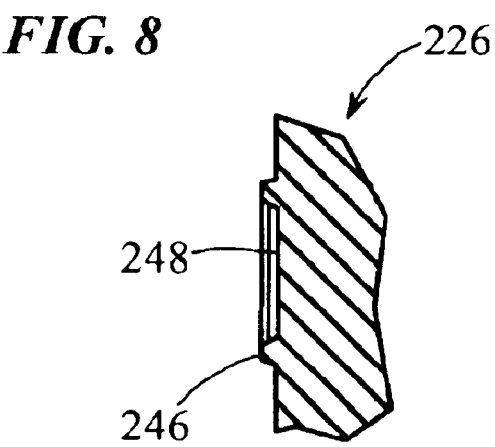
FIG. 8 is an enlarged, partial, cross-sectional view of the resealable portion of FIG. 7 and showing the penetrable portion thereof for receiving a needle or like instrument therethrough.

In the operation of the apparatus 252, and as shown typically in FIG. 9A, each vial is first introduced into the cauterizing station with the penetrable surface region 248 of the resealable member 226 aligned with the heating surface 264. Then, the drive source 272 is actuated to drive the housing 254 downwardly until the peripheral sealing surfaces 262 sealingly engage the upper flange surface 236 of the respective locking member 234, and the heating surface 264 simultaneously engages the exposed penetrable surface portion 248 of the resealable member 226. The heated surface 264 is maintained at a predetermined temperature, and is held in contact with the exposed surface portion 248 for a predetermined time period, sufficient to cauterize the exposed surface portion. One advantage of the construction of the resealable member 226 as shown in FIGS. 7 and 8, is that the cauterization process deforms the annular protuberance 246 into a contour conforming to that of the heated surface, thus allowing an operator (or optical or other automatic sensing system) to visually determine whether each cap has been properly cauterized prior to filling. As shown in FIG. 9C, after cauterizing the exposed surface, the drive source 272 is actuated to drive the housing 254 upwardly and out of engagement with the cap, another vial is moved under the housing, and the process is repeated until all desired vials are cauterized. As described further below, upon exiting the cauterizing station of FIGS. 9A through 9C, the vials are preferably then moved into a filling station to promptly fill the sterilized vials. The cauterization and filling stations are preferably mounted within a sterile enclosure with a laminar gas flow through the enclosure to facilitate maintaining the sterile conditions, as described, for example, the above-mentioned '772 patent.

In the currently preferred embodiment of the present invention, the temperature of the heating surface is within the range of approximately 250° C. to 300° C., and the cycle times (i.e., the time period during which the heating surface is maintained in contact with the exposed surface 248 of the resealable member) are within the range of approximately 1.0 to 3.0 seconds. The present inventor has determined that these temperatures and cycle times may achieve at least approximately a 6 log reduction in bio-burden testing to thereby effectively sterilize the surface.

Figure 10:
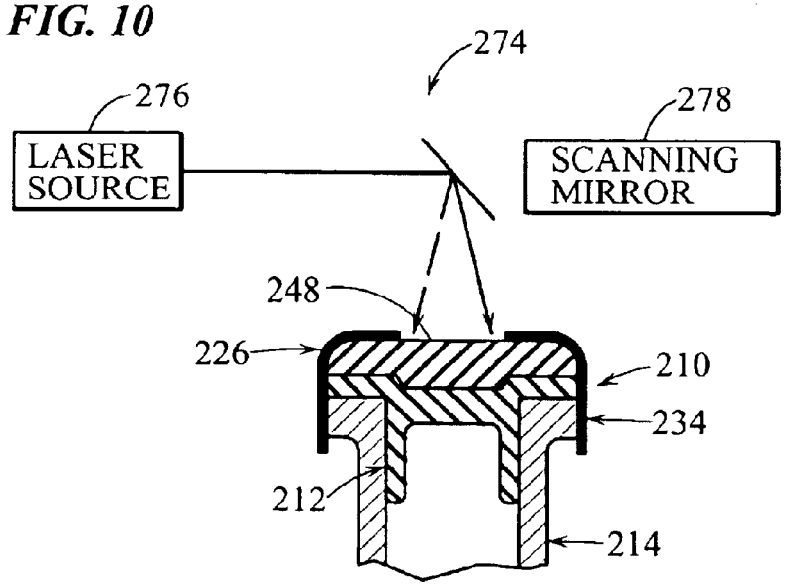
FIG. 10 is a somewhat schematic, partial cross-sectional view of an apparatus used in a method of the present invention for sterilizing the resealable portion of the cap by laser cauterization prior to introducing the filling needle or like instrument therethrough.

In FIG. 10, an alternative apparatus for cauterizing the resealable caps is indicated generally by the reference numeral 274. The apparatus 274 differs from the apparatus 252 of FIGS. 9A through 9C in that the thermal energy required for sterilizing the filling area of the resealable member is supplied by a laser (referred to herein as "laser cauterization"). The laser cauterization apparatus 274 comprises a laser or other suitable radiation source 276 optically coupled to a scanning mirror 278 mounted over the vial/cap assembly. Although not shown in FIG. 10, the vials are preferably mounted within the same type of support as shown in FIGS. 9A through 9C in order to allow the resealable caps to be rapidly cauterized in succession prior to filling each vial with medicament, as described further below.

In the currently preferred embodiment of the present invention, the laser 276 is a commercially available $CO_2$ or YAG laser. The $CO_2$ laser operates at a wavelength of approximately 10.6 $\mu$m. At this wavelength, absorption of the laser energy is governed by the electrical conductivity of the material. Therefore, an insulating material, such as the elastomeric material of the resealable member 226, absorbs and converts most of the incident energy into thermal energy to cauterize the receiving surface 248. The YAG laser operates at wavelength of approximately 1.06 $\mu$m. At this frequency, absorption is governed by the lattice atoms. Thus, a clear or transparent polymer with little ionization would be permeable to the laser beam. Accordingly, when employing a YAG laser, it is desirable to add a colorant to the elastomeric material of the resealable member in a manner known to those of ordinary skill in the pertinent art in order to enhance its absorption of the laser energy. A significant advantage of the YAG laser is that the superficial layer of the penetrable region of the resealable member, and any germs, bacteria or other contaminants thereon, are transformed into plasma to rapidly and thoroughly sterilize the effected surface. If necessary, a UV-filtration coating may be applied to the surfaces of the enclosure for the apparatus of the invention to prevent the operators from receiving any unnecessary UV exposure.

The present inventor has demonstrated that beam energies in the range of approximately 15 to 30 W are sufficient to effectively cauterize the surface 248 of the elastomeric resealable member. In addition, bio-burden testing has demonstrated that laser energies of approximately 20W or greater may achieve a 6.0 log reduction. At these energies, the apparatus of the present invention may effectively sterilize the surface 248 within a cycle time of approximately 0.5 seconds. Accordingly, a significant advantage of the laser cauterization apparatus and method of the present invention is that they may involve significantly shorter cycle times than various direct heat methods. Yet another advantage of the laser cauterization of the present invention, is that it involves both a non-contact method and apparatus, and therefore there is no need to be concerned with the cleaning of a contact head or like heating surface.

Figure 11:
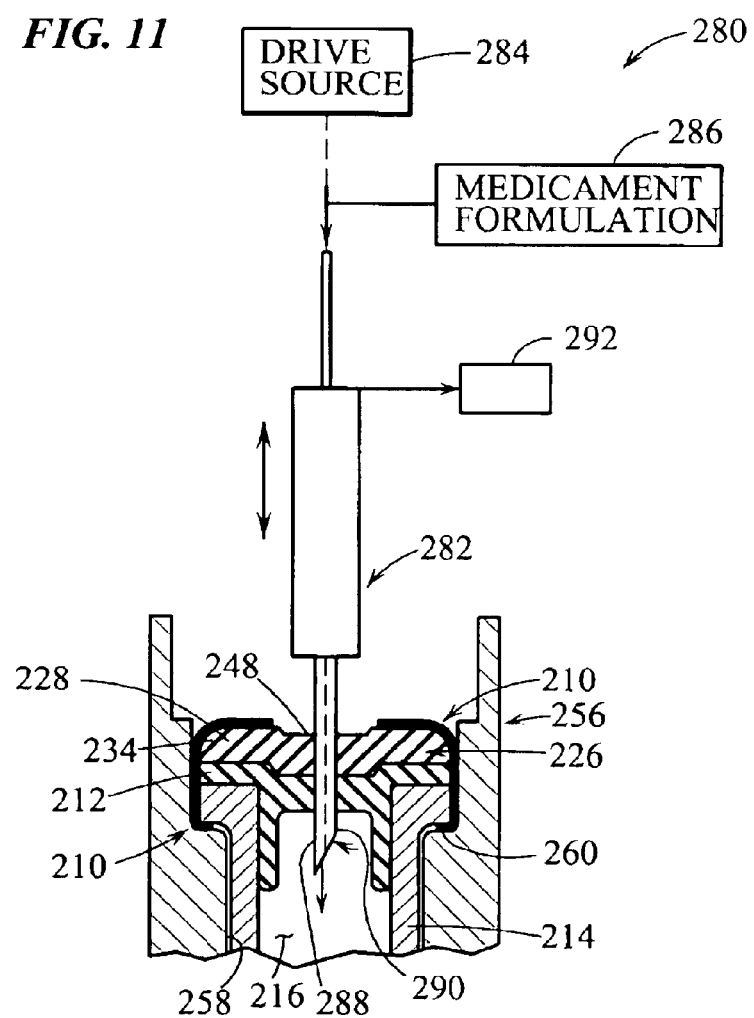
FIG. 11 is a somewhat schematic, partial cross-sectional view of an apparatus used in a method of the present invention for needle filling the assembled cap, vial and locking member with a predetermined medicament.

Turning to FIG. 11, after direct heat or laser cauterization of the resealable member 226 of each vial, the vial is moved within the support 256 (such as by vibratory drive) into a filling station 280. The filling station 280 includes a needle or like injection member 282 reciprocally mounted over the support 256, as indicated by the arrows in FIG. 11, and axially aligned with the penetrable region 248 of the resealable member 226 of each vial/cap assembly passing therethrough. A drive source 284 is drivingly connected to the needle 280 for reciprocally driving the needle 282 into and out of engagement with each cap 210. A medicament or other formulation reservoir 286 is coupled in fluid communication with the needle 282 for introducing a predetermined medicament or other formulation through the needle and into the vial. In the currently preferred embodiment of the present invention, the needle 282 defines a plurality of fluid conduits therein, including a first fluid conduit 288 for injecting the predetermined medicament or other formulation into the vial, as indicated by the arrow in FIG. 11, and a second fluid conduit 290 coupled in fluid communication with a vacuum source 292 for withdrawing air or other gases from the interior cavity 216 of the vial prior to and/or during the filling of the cavity with the medicament or other formulation. In the illustrated embodiment of the present invention, the needle 282 is a "double lumen" needle, defining a central fluid conduit 288 for injecting the predetermined medicament or other formulation into the vial, and an outer annular fluid conduit 290 for drawing the displaced air or other gases out of the interior cavity of the vial.

As shown in FIGS. 12A through 12D, after filling the vial with the medicament or other formulation and withdrawing the needle 282 from the cap 210, the penetrated region of the cap defines a needle hole 294 along the path of the withdrawn needle (FIG. 12B). Upon withdrawing the needle, the vulcanized rubber base 212 of the cap is sufficiently resilient to close upon itself in the penetrated region and thereby maintain the vial in a sealed condition. However, as described above, vapors, gases and/or liquid may be allowed over time to pass through the needle hole, and therefore each vial/cap assembly is passed through a sealing station, as shown typically in FIG. 12C, to heat seal the resealable portion 226 of the cap promptly after withdrawing the needle therefrom. As shown typically in FIG. 12C, a heated member or surface 264 is reciprocally mounted over, and axially aligned with the penetrable region 248 of the vial/cap assembly received within the filling station. A drive source 272 is drivingly connected to the heated member 264 to reciprocally drive the heated member into and out of engagement with the resealable member of each cap. As shown typically in FIG. 12C, the heated member 264 is maintained at a sufficient temperature, and maintained in engagement with the penetrated region of the resealable member 226 to fuse the elastomeric material and hermetically seal the needle hole 294. As a result, and as shown typically in FIG. 12D, the needle hole is eliminated from the exterior region of the resealable member to thereby maintain a hermetic seal between the cap and vial.

As may be recognized by those skilled in the pertinent art based on the teachings herein, the drive source and heating member/surface of FIGS. 12A through 12D may take the form of any of numerous different drive sources and heating members as described above. As indicated typically in FIG. 12C, however, the heating member 264 may define a smaller width than the heating member/surface described above for cauterizing the penetrable region of the cap prior to filling. In addition, the temperature of the heating member 264 for sealing may be higher than that of the heating member described above in order to rapidly melt and seal the penetrated region. One advantage of the resealable cap used in the method of the present invention, is that the underlying rubber base 212 thermally insulates the heated region from the medicament in the vial to thereby maintain the medicament in the vial within an appropriate temperature range throughout the cauterization and heat sealing processes and thereby avoid any thermal damage to the medicament.

Alternatively, and as shown in FIGS. 13A through 13C, the laser source 276 and scanning mirror 278 may be employed to heat seal the penetrated region 294/248 of the resealable member. Accordingly, the same type of laser source 276 and scanning mirror 278 as described above may be employed in the heat sealing station to perform this function, or alternatively, a different type of laser system may be employed. In a currently preferred embodiment of the present invention, a $CO_2$ laser of approximately 50 W is employed to seal a region approximately 0.10 inch in diameter in the resealable cap.

As may be recognized by those skilled in the pertinent art based on the teachings herein, numerous changes and modifications may be made to the above-described and other embodiments of the present invention without departing from its scope as defined in the appended claims. For example, the resealable member may be integrally molded with the base such as by insert molding, the resealable member may be fused or otherwise melted to the base, or the resealable member may be sequentially molded to the base. In addition, the resealable member may be made of any of numerous different materials which are currently known, or which later become known for performing the functions of the resealable member described herein, such as any of numerous different thermoplastic and/or elastomeric materials, including, for example, low-density polyethylene. Similarly, the base can be made of vulcanized rubber as described above, or any of numerous other materials which are currently, or later become known as being compatible with, or otherwise defining a stable enclosure for the particular medicament contained within the vial. In addition, the end cap of the invention may include more than one layer of vulcanized rubber and/or more than one layer of resealable material. In addition, the cauterization and sealing stations used in the method of the present invention may employ any of numerous different types of heat sources that are currently, or later become known, for performing the functions of the heat sources described herein, such as any of numerous different types of laser or other optical sources or conductive heat sources. Accordingly, this detailed description of the preferred embodiments is to be taken in an illustrative, as opposed to a limiting sense.

What is claimed is:

1. A method of filling a vial with a predetermined medicament, comprising the following steps:

providing a vial; a resealable stopper including a body defining a predetermined wall thickness in an axial direction thereof, wherein the body defines a needle penetration region that is pierceable with a needle to form a needle aperture therethrough, and is heat resealable to hermetically seal the needle aperture by applying laser radiation from a laser source at a predetermined wavelength and power thereto; a locking member for securing the stopper to the vial; and a laser source that transmits laser radiation;

selecting a predetermined wavelength and power of the laser source;

selecting a predetermined color and opacity of the needle penetration region of the resealable stopper that substantially absorbs laser radiation at the predetermined wavelength and power to hermetically seal a needle aperture formed in the needle penetration region thereof in a predetermined time period;

selecting the predetermined wall thickness of the body of the resealable stopper to substantially absorb the laser radiation at the predetermined wavelength and substantially prevent the passage of radiation through the predetermined wall thickness of the body;

prior to filling the vial with medicament, assembling the stopper and locking member to the vial and forming a substantially gas-tight seal between the stopper and vial;

sterilizing the empty assembled stopper, locking member and vial;

penetrating the needle penetration region of the body with a needle coupled in fluid communication with a source of the predetermined medicament;

introducing the predetermined medicament through the needle and into the interior of the vial;

withdrawing the needle from the needle penetration region of the body and forming a needle aperture therein;

applying laser radiation from the laser source at the predetermined wavelength and power to the needle penetration region of the body;

substantially absorbing within the needle penetration region of the body the laser radiation at the predetermined wavelength and substantially preventing the passage of radiation through the predetermined wall thickness of the body; and causing the laser radiation at the predetermined wavelength and lower to hermetically seal the needle aperture formed in the needle penetration region of the body within the predetermined time period to form a substantially gas-tight seal between the penetrated region and the interior of the vial.

2. A method as defined in claim 1, wherein the sterilizing step includes engaging the penetrable surface of the needle penetration region of the body with a heated member to sterilize the surface.

3. A method as defined in claim 1, wherein the sterilizing step includes providing a laser source, and transmitting radiation from the laser source onto the penetrable surface of the needle penetration region of the stopper body to sterilize the surface.

4. A method as defined in claim 1, further comprising the step of using the body to thermally insulate the medicament in the vial from the laser energy applied by the laser source to avoid thermal damage to the medicament in the vial.

5. A method as defined in claim 1, wherein the step of providing a resealable stopper includes providing a body defining an underlying portion formed of a first material compatible with the predetermined medicament and defining a medicament-exposed surface exposed to the predetermined medicament within the vial; and a resealable portion overlying the underlying portion, the resealable portion and underlying portion being penetrable by the needle for introducing the predetermined medicament through the stopper and into the vial, wherein the penetrable region of the underlying portion is substantially infusible in response to the application of thermal energy from the laser source, and the penetrable region of the resealable portion is fusible in response to the application of thermal energy from the laser source to form a gas-tight seal between the resealable portion and the medicament in the vial upon removing the needle therefrom.

6. A method as defined in claim 1, wherein the sterilizing step includes achieving an approximately 6 log reduction in bio-burden on the needle penetration region of the stopper.

7. A method as defined in claim 3, further comprising the step of sterilizing the needle penetration region within a cycle time of approximately 0.5 seconds.

8. A method as defined in claim 1, further comprising the step of introducing medicament through a first fluid passageway of the needle, and allowing fluid to flow out of the vial through a second fluid passageway upon introducing medicament from the first fluid passageway into the vial.

9. A method as defined in claim 1, comprising the step of introducing a preservative-free medicament through the needle and into the vial.

10. A method as defined in claim 1, comprising the step of sterilizing the sealed, empty vial by the applying radiation thereto.

11. A method as defined in claim 1, comprising the step of transmitting the laser radiation at a predetermined wavelength of approximately 10.6 µm.

12. A method as defined in claim 1, comprising the step of transmitting the laser radiation at a predetermined wavelength of approximately 1.06 µm.

13. A method as defined in claim 1, comprising the step of transmitting the laser radiation at a predetermined power within the range of approximately 15 to 30 Watts.

14. A method of filling a container with a predetermined substance, comprising the following steps:

providing a container;

providing a laser source that transmits laser radiation at a predetermined wavelength and power;

providing a resealable stopper including a body defining a predetermined wall thickness in an axial direction thereof that substantially absorbs the laser radiation at the predetermined wavelength and power and substantially prevents the passage of such radiation therethrough, and a needle penetration region that is pierceable with a needle to form a needle aperture therethrough and that defines a predetermined color and opacity that substantially absorbs the laser radiation at the predetermined wavelength and power to hermetically seal a needle aperture therein in a predetermined time period;

providing a locking member for securing the stopper to the container;

prior to filling the container with the substance, assembling the stopper and locking member to the container and forming a substantially gas-tight seal between the stopper and container;

penetrating the needle penetration region of the body with a needle coupled in fluid communication with a source of the predetermined substance;

introducing the predetermined substance through the needle and into the interior of the container;

withdrawing the needle from the needle penetration region of the body and forming a needle aperture therein;

applying laser radiation from the laser source at the predetermined wavelength and power to the needle penetration region of the body;

substantially absorbing within the needle penetration region of the body the laser radiation at the predetermined wavelength and power and substantially preventing the passage of radiation through the predetermined wall thickness of the body; and causing the laser radiation at the predetermined wavelength and power to hermetically seal the needle aperture formed in the needle penetration region of the body within the predetermined time period to form a substantially gas-tight seal between the penetrated region and the interior of the container.

15. A method as defined in claim 14, further comprising the step of:

sterilizing the stopper, locking member and container.

16. A method as defined in claim 15, wherein the sterilizing step includes engaging the penetrable surface of the needle penetration region of the body with a heated member to sterilize the surface.

17. A method as defined in claim 15, wherein the sterilizing step includes providing a laser source, and transmitting radiation from the laser source onto the penetrable surface of the needle penetration region of the stopper body to sterilize the surface.

18. A method as defined in claim 14, further comprising the step of using the body to thermally insulate the substance in the container from the laser energy applied by the laser source to avoid thermal damage to the substance in the container.

19. A method as defined in claim 14, wherein the step of providing a resealable stopper includes providing a body defining an underlying portion formed of a first material compatible with the predetermined substance and defining a substance-exposed surface exposed to the predetermined substance within the container; and a resealable portion overlying the underlying portion, the resealable portion and underlying portion being penetrable by the needle for introducing the predetermined substance through the stopper and into the container, wherein the penetrable region of the underlying portion is substantially infusible in response to the application of thermal energy from the laser source, and the penetrable region of the resealable portion is fusible in response to the application of thermal energy from the laser source to form a gas-tight seal between the resealable portion and the substance in the container upon removing the needle therefrom.

20. A method as defined in claim 15, wherein the sterilizing step includes achieving an approximately 6 log reduction in bio-burden on the needle penetration region of the stopper.

21. A method as defined in claim 20, further comprising the step of sterilizing the needle penetration region within a cycle time of approximately 0.5 seconds.

22. A method as defined in claim 14, comprising the step of introducing substance through a first fluid passageway of the needle, and allowing fluid to flow out of the container through a second fluid passageway upon introducing substance from the first fluid passageway into the container.

23. A method as defined in claim 14, comprising the step of introducing a preservative-free substance through the needle and into the container.

24. A method as defined in claim 15, comprising the step of sterilizing the sealed, empty container by the applying radiation thereto.

25. A method as defined in claim 14, comprising the step of transmitting the laser radiation at a predetermined wavelength of approximately 10.6 µm.

26. A method as defined in claim 14, comprising the step of transmitting the laser radiation at a predetermined wavelength of approximately 1.06 µm.

27. A method as defined in claim 14, comprising the step of transmitting the laser radiation at a predetermined power within the range of approximately 15 to 30 Watts.

28. A method as defined in claim 14, wherein the container is a vial, and the substance is a medicament.

* * * * *